United States Patent
Mou et al.

(10) Patent No.: US 11,666,662 B2
(45) Date of Patent: *Jun. 6, 2023

(54) SILICA-BASED BIOMOLECULE CARRIER, PHARMACEUTICAL COMPOSITION COMPRISING THE SAME, PREPARATION METHOD AND USE THEREOF

(71) Applicant: NATIONAL TAIWAN UNIVERSITY, Taipei (TW)

(72) Inventors: Chung-Yuan Mou, Taipei (TW); Yi-Ping Chen, Keelung (TW); Si-Han Wu, Taichung (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 134 days.

This patent is subject to a terminal disclaimer.

(21) Appl. No.: 15/750,759

(22) PCT Filed: Jan. 20, 2016

(86) PCT No.: PCT/US2016/014194
§ 371 (c)(1),
(2) Date: Feb. 6, 2018

(87) PCT Pub. No.: WO2017/023358
PCT Pub. Date: Feb. 9, 2017

(65) Prior Publication Data
US 2018/0228918 A1    Aug. 16, 2018

Related U.S. Application Data

(63) Continuation of application No. 14/819,438, filed on Aug. 6, 2015.

(60) Provisional application No. 62/034,181, filed on Aug. 7, 2014, provisional application No. 62/034,282, filed on Aug. 7, 2014, provisional application No. 62/034,192, filed on Aug. 7, 2014.

(51) Int. Cl.
| | | |
|---|---|---|
| *A61K 47/69* | (2017.01) | |
| *A61K 47/62* | (2017.01) | |
| *A61K 39/385* | (2006.01) | |
| *G01N 33/552* | (2006.01) | |

(52) U.S. Cl.
CPC ........ *A61K 47/6923* (2017.08); *A61K 39/385* (2013.01); *A61K 47/62* (2017.08); *A61K 47/6925* (2017.08); *A61K 47/6929* (2017.08); *G01N 33/552* (2013.01); *G01N 2333/163* (2013.01)

(58) Field of Classification Search
CPC .... A61K 47/6923; A61K 47/50; A61K 47/62; A61K 47/6929
See application file for complete search history.

(56) References Cited

U.S. PATENT DOCUMENTS

| | | |
|---|---|---|
| 2007/0026535 A1 | 2/2007 | Astatke |
| 2007/0281036 A1 | 12/2007 | Landry |
| 2010/0183504 A1* | 7/2010 | Chen .................. A61K 49/0002 424/1.29 |
| 2012/0207795 A1* | 8/2012 | Zink .................... A61K 9/0019 424/400 |
| 2013/0145488 A1 | 6/2013 | Wang |
| 2014/0134700 A1 | 5/2014 | Lu |
| 2014/0275509 A1 | 9/2014 | Del Pino González De La Higuera et al. |
| 2016/0038608 A1* | 2/2016 | Mou .................... G01N 33/552 435/375 |
| 2016/0041153 A1 | 2/2016 | Brown et al. |

FOREIGN PATENT DOCUMENTS

| | | |
|---|---|---|
| JP | 2014-522993 A | 9/2014 |
| WO | 2013022995 A2 | 2/2013 |
| WO | 2015042279 A1 | 3/2015 |

OTHER PUBLICATIONS

Chen Yi-Ping (Chen I). (Biomedical Application of Mesoporous Silica Nanoparticles: Enzymes Delivery and Target Therapy. 2013, Degree these of Institute of Chemistry Taiwan University. Retrieved from https://www.airitilibrary.com/Publication/alDetailedMesh?docid=U0001-3007201318313400, Mar. 16, 2016) (Year: 2013).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Guido et al. Virtual Screening and Its Integration with Modern Drug Design Technologies. Curr Med Chem. 2008; 15(1):37-46 (Year: 2008).*
Clark et al. Discovery and Development of Janus Kinase (JAK) Inhibitors for Inflammatory Diseases. J. Med. Chem., 2014, 57 (12), pp. 5023-5038 (Year: 2014).*
Aagaard et al. RNAi therapeutics: Principles, prospects and challenges. Advanced Drug Delivery Reviews; 2007;59: 75-86 (Year: 2007).*
Warzocha et al. Antisense strategy: biological utility and prospects in the treatment of hematological malignancies. Leukemia and Lymphoma, 1997;24: 267-281 (Year: 1997).*
Demarchi et al. Activation of Transcription Factor NF-kB by the Tat Protein of Human Immunodeficiency Virus Type 1. J Virol. Jul. 1996; 70(7): 4427-4437 (Year: 1996).*

(Continued)

*Primary Examiner* — Vanessa L. Ford
*Assistant Examiner* — Sandra Carter
(74) *Attorney, Agent, or Firm* — Duane Morris LLP

(57) ABSTRACT

Silica-based biomolecule carriers, compositions comprising the same and preparation methods and uses thereof for delivering biomolecules into a cell are provided. The silica-based biomolecule carrier comprises a porous core; a first bioactive moiety; a second bioactive moiety functionally associated with the first bioactive moiety; and linkers for respectively conjugating the first bioactive moiety and the second bioactive moiety to the porous core.

12 Claims, 6 Drawing Sheets
Specification includes a Sequence Listing.

(56) References Cited

OTHER PUBLICATIONS

Li et al. Dasatinib blocks cetuximab-and radiation-induced nuclear translocation of the epidermal growth factor receptor in head and neck squamous cell carcinoma. Radiother Oncol. Nov. 2010; 97(2): 330-337 (Year: 2010).*

Chen Yi-Ping. (Biomedical Application of Mesoporous Silica Nanoparticles: Enzymes Delivery and Target Therapy. 2013, Degree these of Institute of Chemistry Taiwan University. Retrieved from https://www.airitilibr8rv.com/Pubncation/alDetayedMeshPdodd-U0001-3007201318313400, Mar. 16, 2016) (Year: 2013).*

Tsai et al. Monoclonal antibody-functionalized mesoporous silica nanoparticles (MSN) for selective targeting breast cancer cells. J. Mater. Chemi,. 2009, 19:5737-5743 (Year: 2009).*

Pan et al. Nuclear-Targeted Drug Delivery of TAT Peptide-Conjugated Monodisperse Mesoporous Silica Nanoparticles. J. Am. Chem. Soc. 2012, 134(13):5722-5725. (Year: 2012).*

Bowie et al. Deciphering the Message in Protein Sequences: Tolerance to Amino Acid Substitutions. Science, 1990, 247:1306-1310 (Year: 1990).*

Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138 (Year: 1990).*

Lazar et al. Transforming Growth Factor ox: Mutation of Aspartic Acid 47 and Leucine 48 Results in Different Biological Activities. Mol. Cell. Biol., 8:1247-1252, 1988 (Year: 1988).*

Bork. Powers and Pitfalls in Sequence Analysis: The 70% Hurdle. Genome Research, 2000, 10:398-400 (Year: 2000).*

Vajdos et al. Comprehensive Functional Maps of the Antigenbinding Site of an Anti-ErbB2 Antibody Obtained with Shotgun Scanning Mutagenesis. J Mol Biol. Jul. 5, 2002;320(2):415-28 (Year: 2002).*

Brown et al.Tolerance to Single, but Not Multiple, Amino Acid Replacements in Antibody V, CDR2. J Immunol. May 1996; 156(9): 3285-91 (Year: 1996).*

Bharti, Charu et al. (2015). Mesoporous Silica Nanoparticles in Target Drug Delivery System: A review. Int J Pharm Investig. Jul.-Sep.; 5(3): 124-133.

Bimbo, Luis Maria. (2012). Biocompatibility and biofunctionalization of mesoporous silicon particles. Academic Dissertation. University of Helsinki, 62 pages.

McCord, Joe M. et, al, (1969). Superoxide Dismutase: An Enzymic Function for Erythrocuprein (Hemocuprein). The Journal of Biological Chemistry, 244, 6049-6055.

International Search Report in International Application No. PCT/US2016/014194, dated Mar. 29, 2016, in 3 pages.

Wu, Si-Han et al. (2013), Synthesis of Mesoporous Silica Nanoparticles, Chem. Soc. Rev., 42, 3862-3875.

Extended European Search Report in EP Counterpart Application No. 16833417.5, dated Mar. 20, 2019, in 9 pages.

Pan et al: "MSN-Mediated Sequential Vascular-to-Cell Nuclear-Targeted Drug Delivery for Efficient Tumor Regression", Advanced Materials, vol. 26, No. 39, Aug. 26, 2014 (Aug. 26, 2014), pp. 6742-6748.

Pan et al: "Supporting Information: MSN-Mediated Sequential Vascular-to-Cell Nuclear-Targeted Drug Delivery for Efficient Tumor Regression", Advanced Materials, vol. 26, No. 39, Aug. 26, 2014 (Aug. 26, 2014), pp. 6742-6748.

Chen et al: "A New Strategy for Intracellular Delivery of Enzyme Using Mesoporous Silica Nanoparticles: Superoxide Dismutase", Journal of the American Chemical Society, vol. 135, No. 4, Jan. 5, 2013 (Jan. 5, 2013), pp. 1516-1523.

Wu et al: "Enzyme-Functionalized Silica Nanoparticles as Sensitive Labels in Biosensing", Analytical Chemistry, vol. 81, No. 4, Jan. 13, 2009 (Jan. 13, 2009), pp. 1600-1607.

Lin et al: "Approach To Deliver Two Antioxidant Enzymes with Mesoporous Silica Nanoparticles into Cells", ACS Applied Materials & Interfaces, vol. 8, No. 28, Jun. 29, 2016 (Jun. 29, 2016) pp. 17944-17954.

Office Action in China Counterpart Application No. 201680046902.6, dated Jul. 29, 2019, in 15 pages; English translation provided.

Office Action in Japan Counterpart Application No. 2018-506167, dated Dec. 3, 2019, in 5 pages; English translation provided.

Office Action in Canada Counterpart Application No. 2,994,809, dated Mar. 25, 2022, in 5 pages.

* cited by examiner

SEQUENCE LISTING

```
<160> NUMBER OF SEQ ID NOS: 2

<210> SEQ ID NO 1
<211> LENGTH: 11
<212> TYPE: PRT
<213> ORGANISM: artificial sequence
<220> FEATURE:
<223> OTHER INFORMATION: synthetic polypepetide

<400> SEQUENCE: 1

Cys Gly Arg Lys Lys Arg Arg Gln Arg Arg Arg
1               5                   10

<210> SEQ ID NO 2
<211> LENGTH: 9
<212> TYPE: PRT
<213> ORGANISM: artificial sequence
<220> FEATURE:
<223> OTHER INFORMATION: synthetic polypeptide

<400> SEQUENCE: 2

Arg Lys Lys Arg Arg Gln Arg Arg Arg
1               5
```

SILICA-BASED BIOMOLECULE CARRIER, PHARMACEUTICAL COMPOSITION COMPRISING THE SAME, PREPARATION METHOD AND USE THEREOF

CROSS-REFERENCE TO RELATED APPLICATIONS

This application is a § 371 national stage entry of International Application No. PCT/US2016/014194, filed Jan. 20, 2016, which is a continuation of U.S. Non-Provisional patent application Ser. No. 14/819,438, filed Aug. 6, 2015, which claims benefit of priority to U.S. Provisional patent application Ser. No. 62/034,181, filed Aug. 7, 2014, U.S. Provisional patent application Ser. No. 62/034,192 filed Aug. 7, 2014, and U.S. Provisional patent application Ser. No. 62/034,282, filed Aug. 7, 2014, the contents of each of which are incorporated by reference herein in their entirety.

The instant application contains a Sequence Listing which has been submitted electronically in ASCII format and is hereby incorporated by reference in its entirety. Said ASCII copy, created Aug. 21, 2020, is named G4590-02900_SL.txt and is about 1 kilobyte in size.

BACKGROUND OF THE INVENTION

1. Field of the Invention

The present invention generally relates to a biomolecule carrier and particularly to silica-based biomolecule carriers, compositions comprising the same and preparation methods and uses thereof.

2. Description of Related Art

To address the poor solubility and other delivery problems of drugs and biomolecules, various carriers have been developed in the past decade, in the hopes of delivering therapeutic agents to the target site in the body. For example, silica-based carriers, such as hollow silica nanospheres (HSNs) and mesoporous silica nanoparticles (MSNs), are suitable delivery reagents for their favorable chemical properties, thermal stability, and biocompatibility.

Drug- or biomolecule-conjugated silica-based materials derived from HSNs or MSNs are among the most promising ways for cancer therapy and the treatment of various challenging diseases. In addition, silica-based carriers may also be useful in enzyme replacement therapy (ERT), which is a medical treatment replacing an enzyme in patients without or with only insufficient that particular enzyme.

However, due to the limitations of some existing approaches, particularly regarding cellular uptake, targeting and delivery issues, there is a need to explore more satisfactory solutions.

SUMMARY OF THE INVENTION

According to embodiments of the present invention, carriers for delivering biomolecules into a cell are provided. The biomolecule carriers comprise silica-based porous cores, such as mesoporous silica nanoparticles (MSNs), and biomolecules conjugated to the silica-based porous cores via linkers, thereby forming silica-based biomolecule carriers having a first bioactive moiety and a second bioactive moiety. The first bioactive moiety and the second bioactive moiety are different from yet functionally associated with each other and may be independently selected from an enzyme, an antibody, a catalytic mimetic, a ligand, a hormone, a biomolecule-binding protein, and a functional fragment thereof, such as a peptide or polypeptide.

According to embodiments of the present invention, a pharmaceutical composition comprising a plurality of aforesaid silica-based biomolecule carriers is disclosed.

According to embodiments of the present invention, a method of preparing an aforesaid composition is disclosed, the method comprising: providing a silica-based carrier having a porous core; forming linkers on the porous core; conjugating first biomolecules to the porous core via at least a part of the linkers; and conjugating second biomolecules functionally associated with the first biomolecules to the porous core via at least a part of the linkers.

Moreover, according to embodiments of the present invention, disclosed is a method of using a composition comprising the aforesaid silica-based biomolecule carriers in the manufacture of a medicament for the treatment of a disease or condition associated with cellular disorders, including but not limited to enzyme deficiency, enzyme defect, cancer, and metabolic disorder. For example, firstly, silica-based biomolecule carriers are prepared and provided. The silica-based biomolecule carriers comprise porous cores and at least two different and functionally-associated bioactive moieties formed from biomolecules conjugated with the porous cores through linkers. Then the silica-based biomolecule carriers are allowed to be in contact with cells by incubating the cells with the carriers. The two different and functionally-associated biomolecules are thus co-delivered into the cells at the same time.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
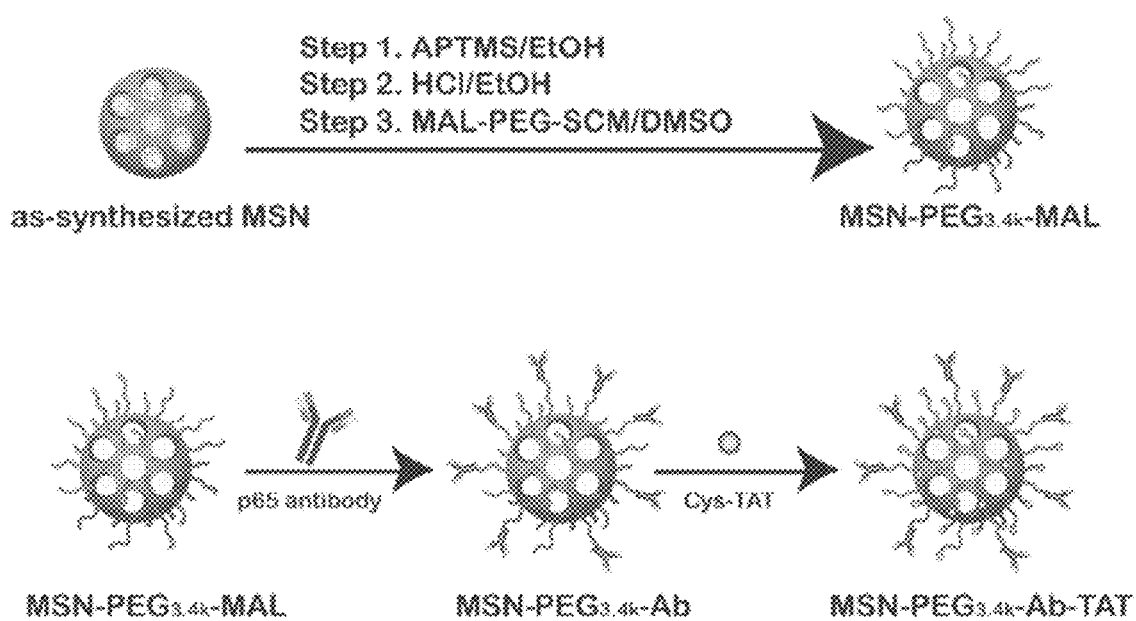
FIG. 1 illustrates the reaction scheme for the conjugation of NF-κB p65 antibody and Cys-TAT peptide to the surface functionalized porous core.
Figure 2A:
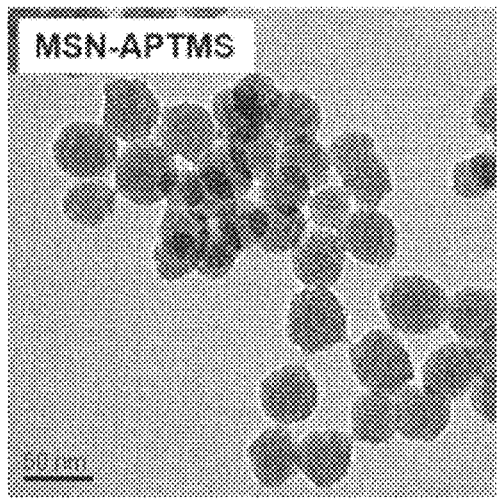
FIGS. 2A-2D show transmission electron microscopy (TEM) images of various functionalized MSNs.
Figure 2B:
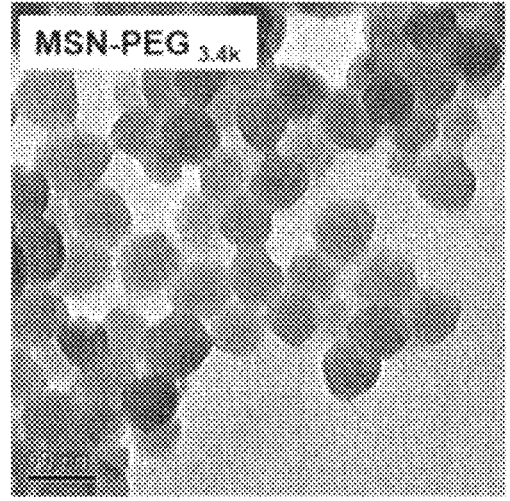
Figure 2C:
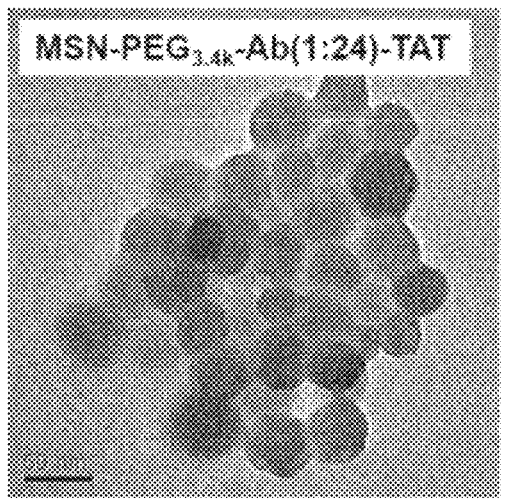
Figure 2D:
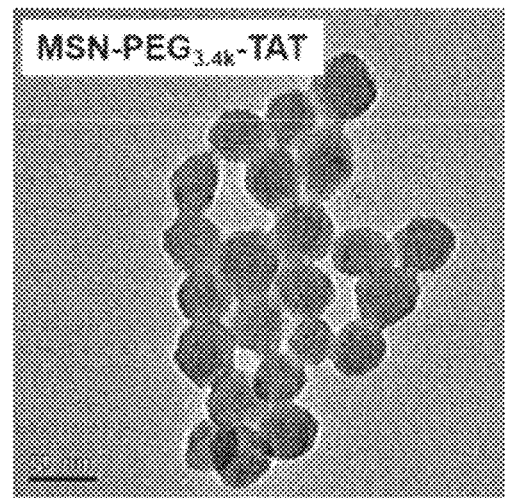

Reference will now be made in detail to the preferred embodiments of the invention, examples of which are illustrated in the accompanying drawings. In the following embodiments, one or more silica-based biomolecule carriers are described. The cited examples, the ingredients, the reaction conditions or parameters illustrated in the examples are merely for illustration purposes and are not intended to limit the material or the preparation method by the exemplary embodiments described herein.

In some embodiments, at least two different biomolecules, such as a first biomolecule and a second biomolecule, are conjugated with a silica-based porous core to act as at least two different bioactive moieties, such as a first bioactive moiety and a second bioactive moiety, of the silica-based biomolecule carrier thus formed. The two biomolecules or bioactive moieties are different from but functionally associated with each other and are conjugated with the porous core by one or more linkers.

As used herein, the term "biomolecule carrier" is intended to mean a micro-scaled or nano-scaled particle, sphere or biological vehicle, such as a porous core, carrying functional biomolecules. As used herein, the term "biomolecule" encompasses any molecule that is (1) present in living organisms, including large macromolecules such as proteins, carbohydrates, lipids, and nucleic acids, as well as small molecules such as primary metabolites, secondary metabolites, and natural products; or (2) not present in living organisms, including artificial or synthetic products, such as modified natural molecules, drugs or bioactive materials.

As used herein, the term "bioactive moiety" refers to the bioactive unit, part, block, region, or domain of the biomolecule carrier, which is formed by the conjugation of a biomolecule to the porous core. The bioactive moiety may be for example biologically active, diagnostic, therapeutic, and prophylactic molecules having an effect on a living organism, tissue or cell. The bioactive moiety may be formed by the conjugation between a porous core and a biomolecule, such as an enzyme, an antibody, a catalytic mimetic, a ligand, a hormone, a biomolecule-binding protein, and a functional fragment thereof. For example, bioactive moieties may be formed from synthetic, recombinant or isolated peptides and proteins such as antibodies, antigens, synthetic small molecule peptidomimetics, receptor ligands, enzymes, adhesion peptides, nucleotides, polynucleic acids such as DNA and antisense nucleic acid molecule, activated sugars and polysaccharides, and organic drug molecules.

In one embodiment, the bioactive moiety is a therapeutic moiety formed by the conjugation of a porous core with a wide variety of biomolecules that are directly or indirectly effective in the treatment or prevention of a disease or clinical condition. Suitable therapeutic moieties may be selected based on the application of the silica-based biomolecule carrier. For example, suitable therapeutic moieties may be found among anti-cancer substances. Preferably, therapeutic moieties are stable entities that retain their therapeutic/biological activity when conjugated to a porous core, including under in vitro and in vivo conditions. Examples of suitable therapeutic moieties are small molecules, proteins, peptides, saccharides, steroids, antibodies, including fragments and variants thereof, fusion proteins, antisense polynucleotides, ribozymes, small interfering RNA, and the like.

When two or more biomolecules are conjugated to the porous core, preferably the bioactive moieties of the silica-based biomolecule carrier are functionally associated with each other. In the present context, the term "functionally associated" should be broadly interpreted and means that one moiety is advantageous or useful to the other in terms of performing its biological function. For example, if two biomolecules are carried, the first moiety is functionally associated with the second moiety if the first moiety provides a function, such as cell penetration or targeting, to promote the second moiety to perform its function more effectively or efficiently. Alternatively, the first moiety is functionally associated with the second moiety if the first moiety and the second moiety are involved in different steps of a biological cascade reaction.

Preferably, the first moiety may be derived from cellular uptake facilitating molecules, such as cell penetrating peptides, positively charged polypeptides, or polyethylenimine; nuclear localization sequence peptides; endosomal targeting peptides; organelle targeting molecules; cancer cell targeting molecules, including ligands, peptides, antibodies, and aptamers; and enzymes involved in a cascade reaction.

Preferably, the second moiety may be derived from biomolecules with cellular regulation activity, such as enzymes involved in a cascade reaction. Preferably, the second moiety may be derived from biomolecules involved in metabolic disorders, including but not limited to lysosomal storage disorders, including Fabry disease, Schindler disease, Gaucher disease (type 1, type 2 and type 3), Pompe disease, Danon disease MPS I (Hurler, Hurler-Scheie, or Scheie syndrome), MPS II (Hunter disease), MPS III (type A, B, C and D), MPS IV (type A and B), MPS VI (Maroteaux-Lamy syndrome), MPS VII (Sly syndrome), MPS IX (hyaluronidase deficiency), Krabbe disease, Farber disease, Galactosialidosis, GM1 gangliosidosis, GM2 gangliosidosis AB variant, Sandhoff disease, Tay-Sachs disease, lysosomal acid lipase deficiency, Niemann-Pick disease (type A, type B, and type C), metachromatic leukodystrophy (MLD), multiple sulfatase deficiency, mucolipidosis (type I, type II, type III and type IV), neuronal ceroid lipofuscinoses (type 1 to 10), Wolman disease, alpha-mannosidosis, beta-mannosidosis, aspartylglucosaminuria, fucosidosis, cystinosis, pycnodysostosis, sialic acid storage disease, infantile free sialic acid storage disease (ISSD), cholesteryl ester storage disease, galactosemia, maple syrup urine disease, phenylketonuria (PKU), glycogen storage disease, mitochondrial disorders, Friedreich ataxia, peroxisomal disorders, including Zellweger syndrome and adrenoleukodystrophy, metal metabolism disorders, including Wilson disease and hemochromatosis, organic acidemias, and urea cycle disorders.

In some embodiments, the second moiety may be derived from biomolecules involved in neoplasms, including with limitation those listed in PCT patent application publication WO 2015/042279 A1, also published as US 2016/0338954 A1, which is hereby incorporated by reference in its entirety. In some embodiments, the biomolecules can be selected from: panitumumab, oregovomab, ofatumumab, zanolimumab, ticilimumab, ipilimumab, bevacizumab, rituximab, trastuzumab, cetuximab, gemtuzumab, alemtuzumab, ibritgumomab, tositumomab, alemtuzumab, Ibritumomab, and Nofetumomab.

In one embodiment, the first bioactive moiety is a transcription factor antibody, and the second bioactive moiety is a nucleus-targeting biomolecule or a cell-penetrating biomolecule. In one embodiment, the first bioactive moiety and the second bioactive moiety are different enzymes or enzyme fragments involved in reactive oxygen species (ROS) metabolism. In another embodiment, the first bioactive moiety and the second bioactive moiety may be in a denatured form or a partially active form before administration to a recipient such as human and may refold after administration.

In one embodiment, at least one of the first bioactive moiety and the second bioactive moiety contains a cell-penetrating domain.

In some embodiments, biomolecules suitable for being carried by the silica-based biomolecule carriers may include an enzyme containing cysteine (thiol group), lysine (amino group), aspartate or glutamate (carboxyl group), a peptide containing cysteine (thiol group), lysine (amino group), aspartate or glutamate (carboxyl group), or an antibody containing cysteine (thiol group), lysine (amino group), aspartate or glutamate (carboxyl group). Alternatively, biomolecules suitable for being carried by the silica-based biomolecule carriers may include an enzyme containing polyhistidine-tag (His-tag), a peptide containing polyhistidine-tag or an antibody containing polyhistidine-tag. Herein, the polyhistidine-tag consists of at least six histidine (His) residues.

The enzymes may be antioxidant enzymes, including horseradish peroxidase (HRP), superoxide dismutase (SOD), catalase (CAT), glutathione peroxidase, glutathione reductase and their enzymatic mimetics or fragments. Alternatively, the enzymes may be enzymes involved in biochemical enzymatic cascades, which refers to a series of biochemical reactions involving enzymes, such as blood coagulation, metabolism pathways, and signal transduction pathways.

According to the present disclosure, biomolecules to be carried by the silica-based biomolecule carrier are conjugated to the porous core. As used herein, the term "conjugated to," "conjugated with," "conjugate" or similar expression refers to two or more chemical or biological entities being linked by a direct or indirect covalent or non-covalent interaction. In some embodiments, the association is covalent. In some embodiments, a covalent association is mediated by a linker moiety. In some embodiments, an association is non-covalent, such as affinity interactions, charge interactions, hydrophobic interactions, metal coordination, hydrogen bonding interactions, van der Waals interactions, magnetic interactions, electrostatic interactions, or dipole-dipole interactions, which are all effectuated or mediated by a linker. Exemplary methods of conjugating biomolecules to silica-based porous cores via linkers can be found from "Bioconjugate Techniques" written by Greg T. Hermanson, 3$^{rd}$ Edition (Sep. 2, 2013), published by Academic Press, which is hereby incorporated by reference in its entirety.

According to the present invention, linkers are employed to form conjugation between biomolecules and the porous core. In one embodiment, a plurality of the same type of linkers are used for forming conjugation, and a first bioactive moiety and a second bioactive moiety may be linked by the same linker or by different linkers of the same type. In one embodiment, two or more different types of linkers are used for forming conjugation, and different bioactive moieties may be linked by different linkers randomly or in a controlled manner.

As used herein, the term "linker," also known as "spacer" or "crosslinking agent," should be broadly interpreted to include any forms of chemical or physical linkage between a core and a biomolecule carried thereby. For example, a silica-based porous core may be functionalized or modified to form a linker thereon. Surface properties of porous cores can be altered during the preparation, or post-synthetic strategies can be employed after the preparation to form linkers. Active surface enables the silica-based porous cores to link biomolecules. The functionalized surface of porous cores with cell-recognition or other site-directing biomolecules produces as an ideal agent for cell tracing or targeting. For example, surface modification or functionalization with targeting ligands, such as folic acid, may be used to enhance specific uptake by cancer cells compared to non-cancerous cells. Useful approaches for modification or functionalization of silica-based porous cores can be found from "Biocompatibility and Biofunctionalization of Mesoporous Silicon Particles", PhD dissertation by Luis Maria Bimbo, University of Helsiniki (2012), which is hereby incorporated by reference in its entirety.

In addition to the linkage function, linkers disclosed in the present invention may preferably have one or more functional segments to provide desirable properties to the silica-based biomolecule carrier, such as purification feasibility, bioavailability, bio-distribution, target specificity, cellular uptake and so on.

In one embodiment, a biomolecule is conjugated by a linker to a silica-based porous core. First, the porous core is functionalized by a reagent such as 3-aminopropyltrimethoxysilane (APTMS) to provide a reactive amino group on the surface of the porous core. Then the amino group is covalently bonded with a polyethylene glycol (PEG) derivative having for example a succinimidyl group and a maleimidyl group, such that this PEG linker is grafted onto the porous core through the reaction between the succinimidyl group and the amino group, and the maleimidyl group may be useful for forming linkage with the biomolecule through the reaction between the maleimidyl group of the linker and the thio group of the biomolecule. In this embodiment, a heterobifunctional PEG derivative is used as the linker to provide advantages such as water solubility, biocompatibility, and length flexibility to the linker. Generally, a heterobifunctional PEG derivative may have a general structure of X-PEG-Y, wherein X and Y are two different functional or reactive groups. Some useful PEG linkers include but not limited to HO-PEG-COOH, HO-PEG-NHS, HS-PEG-SGA, $NH_2$-PEG-COOH, MAL-PEG-NHS, biotin-PEG-MAL, and alkyne-PEG-MAL. Different X and Y can be selected according to the properties of the porous cores and the biomolecules to be carried. In addition, the length or molecular weight of the PEG linker may be chosen according to the type of porous cores and biomolecules as well as the end use or application of the silica-based biomolecule carriers thus formed.

In another embodiment, a molecule containing a bivalent metal ion, such as a nickel or cobalt ion, is used as the linker. For example, a porous core may be treated with nitrilotriacetic acid-containing silane (NTA-silane) and then with $NiCl_2$ to provide nickel ions on the surface of the porous core for binding biomolecules having polyhistidine-tag. The bivalent metal ion approach is more advantageous when the biomolecules to be immobilized on the porous core are genetically modified proteins or polypeptides. Alternatively, the porous cores may also be treated by $Ni^{2+}$:NTA-PEG derivatives to form linkers with a PEG segment and a bivalent metal ion.

In another embodiment, the linker may comprise a first terminal linked to the porous core, a second terminal linked to the first or second bioactive moiety, and a functional segment between the first terminal and the second terminal for facilitating cellular uptake. The selection of the type, molecular weight, and biological property of linkers present in the silica-based biomolecule carrier to achieve desired delivery functions can be determined without undue experimentations.

As used herein, the term "porous core" or "core" generally refers to a nano-scaled particle, sphere or biological vehicle capable of carrying functional biomolecules. Unless specified otherwise, the term "porous core" or "core" may be used interchangeably with "mesoporous silica nanoparticle" (MSN), referring to a mesoporous form of the silica particle. The large surface area of the porous core allows the particles to be useful for biomolecule delivery.

Abundant successful syntheses of various silica-based porous cores have been reported thus far. For example, MSNs may be synthesized by reacting tetraethyl orthosilicate with a template made of micellar rods. The result is a collection of nano-sized spheres or rods that are filled with a regular arrangement of pores. The template can then be removed by washing with a solvent adjusted to a proper pH. In another process, MSNs could be synthesized using a simple sol-gel method or a spray drying method. Tetraethyl orthosilicate is also used with an additional polymer monomer (as a template). Other methods include fast self-assembly, soft and hard templating, a modified Stober method, dissolving-reconstruction and modified aerogel approaches. Several different synthesis methodologies to prepare porous cores can be found from for example "Synthesis of Mesoporous Silica Nanoparticles," Si-Han Wu et. al., Chem. Soc. Rev., 2013, 42, 3862-3875, and "Mesoporous Silica Nanoparticles in Target Drug Delivery System: A review," Charu Bharti et. al., Int J Pharm Investig. 2015 July-September; 5(3): 124-133, which are hereby incorporated by reference in its entirety. Preferably, suitable synthesis methodologies are chosen such that good control of the morphology, particle size, uniformity and/or dispersity is achieved.

In one embodiment, the porous core has an average pore size of 2 to 50 nm, such as 5 to 50 nm, 10 to 50 nm, 20 to 50 nm, 2 to 5 nm or 2 to 10 nm. In one embodiment, the porous core has a particle size or diameter of less than 300 nm, such as less than 250 nm, less than 200 nm, less than 150 nm, or less than 100 nm, for example between 2 and 300 nm, between 2 and 200 nm, between 10 and 200 nm, or between 50 and 100 nm.

Depending on different needs or applications, the size of the porous core may be controlled. This tunability of pore size provides the opportunity to carry biomolecules ranging from small-molecular drugs up to macromolecules, such as proteins and enzymes.

In one embodiment, size-dependent uptake in cell lines, as well as tissue distribution, has been observed for silica nanoparticles. Bio-distribution and clearance of particles in vivo are highly dependent on their physical and chemical characteristics. The gas, such as nitrogen, adsorption technique may be used to measure the pore size distribution of materials. Transmission electron microscopy (TEM) and dynamic light scattering (DLS) may be used to measure the size of nanoparticles in dried and in aqueous media, respectively.

Preferably, during or after the preparation, the porous core may be functionalized to provide desirable properties according to the needs. For example, the porous core may be functionalized with amino groups, nitrilotriacetic acid, polyethylene glycol, fluorescent tags or a combination thereof.

Accordingly, the silica-based biomolecule carriers made according to the present invention may be useful for the preparation of a pharmaceutical composition in which an effective amount of silica-based biomolecule carriers are dispersed in a biological medium, such as a pharmaceutically or physiologically acceptable diluent for administration to a recipient in need, for example, water or saline.

Alternatively, in another embodiment, mesoporous silica nanoparticle (MSN) materials are synthesized and functionalized to carry peptides and/or antibodies. The peptides may be any peptide containing cysteine or a polyhistidine tag, including nucleus localization sequence (NLS)-peptides, cancer-targeting peptides and lysosomal targeting peptides. The antibodies may be any antibody containing cysteine or a polyhistidine tag, including signal transduction antibodies and cancer-targeting antibodies.

The present invention provides nanoparticles consisting of mesoporous silica nanoparticle (MSN) with surface functionalization of NF-κB (nuclear factor-kappa B) p65 antibody and TAT transducing peptide (i.e., HIV trans-activator of transcription (TAT) protein transduction domain). The sequence of TAT transducing peptide: CGRKKRRQRRR (SEQ ID NO: 1). These nanoparticles can move near nuclear membrane and block nuclear translocation of the activated p65.

FIG. 1 illustrates the reaction scheme for the conjugation of NF-κB p65 antibody and Cys-TAT peptide to the surface functionalized MSN. To synthesize the functionalized MSN, amine groups are formed on the surface of MSN by reacting with 3-aminopropyltrimethoxysilane (APTMS) to form MSN-APTMS with an average loading of nitrogen content of APTMS at 2.6 wt % by elemental analysis. In order to immobilize p65 antibody on MSN, two polyethylene glycol (PEG) linkers with different lengths were chosen, MAL-PEG$_{2k}$-SCM and MAL-PEG$_{3.4k}$-SCM, to react with MSN-APTMS. Herein, the abbreviations are explained, MAL: maleimide, PEG$_{2k}$ or PEG$_{3.4k}$: polyethylene glycol (PEG) having an average molecular weight of 2000 or 3400, SCM: succinimidyl carboxymethyl. The MAL-PEG-SCM linkers contain a succinimidyl moiety reactive with the amine groups of MSN-APTMS through an active succinimidyl linkage to obtain the MSN-PEGs (MSN-PEGs: MSN-PEG$_{2k}$, MSN-PEG$_{3.4k}$). The MAL-end of MSN-PEG reacted with the thiol groups of the antibody and Cys-TAT peptide.

Synthesis of Green Fluorescent Mesoporous Silica Nanoparticles (MSN)

C$_{16}$TABr (0.58 g, 1.64×10$^{-3}$ mole) and 5 mL of 0.226 M ethanol solution of tetraethoxysilane (TEOS, 1 mL TEOS in 20 mL 99.5% ethanol) were dissolved in 300 g of 0.17 M aqueous ammonia solution. The stock solution was stirred at 40° C. for 5 h. 5 mL of 1.13 M ethanol solution of TEOS (5 mL of TEOS in 20 mL 99.5% ethanol) and FITC-APTMS were added with vigorous stirring for 1 h and then aged statically at 40° C. for 24 h. FITC-APTMS, N-1-(3-trimethoxysilyl propyl)-N'-fluoreceylthiourea), was prepared in advance by stirring fluorescein isothiocyanate (FITC, 1 mg) and 3-aminopropyltrimethoxysilane (APTMS, 100 μL) in 5 mL ethanol (99%) at room temperature for 24 h. As synthesized samples were then collected by centrifugation with 12000 rpm for 20 min and washed five times with 99% ethanol. 200 mg of as-synthesized samples were redispersed in 25 mL of 95% ethanol with 0.5 g of 37 wt % HCl. Surfactant was extracted by heating the ethanol suspension at 60° C. for 24 h. The product, called FITC-MSN, was collected by centrifugation and washed with ethanol several times and stored in ethanol.

Preparation of Amine-Functionalized MSN (MSN-APTMS)

The surface of MSN was functionalized with amine groups by treatment with APTMS. MSNs (200 mg) were first dispersed in 50 mL of ethanol, and then the solution was refluxed for 18 h after the addition of 500 μL of APTMS. After centrifugation and washing with ethanol, amine-functionalized MSNs were redispersed in ethanol. To remove the surfactants, the amine-functionalized MSNs were suspended in acidic ethanol (1 g of HCl in 50 mL of EtOH) and refluxed for 24 h. After centrifugation and washing with ethanol, amine-functionalized MSN (MSN-APTMS) were redispersed in ethanol.

Transmission Electron Microscopy (TEM)

TEM images were taken using a Hitachi H-7100 instrument with an operating voltage of 75 KV. Samples were sonicated to disperse in ethanol, and 10 µL of the suspension was dropped to fix on a microgrid.

For evaluation of immunological efficiency, the p65 antibody was covalently immobilized with the MAL-end of MSN-PEG$_{3.4k}$ in different ratios (1:6, 1:12, 1:24) via C—S binding. After the p65 antibody conjugation, the Cys-TAT peptide was conjugated to fill up the free MAL-end of MSN-PEG$_{3.4k}$. MSN-PEG$_{3.4k}$ without antibody coupling was also directly conjugated with Cys-TAT as a control. The physical properties of the nanoparticles were characterized by nitrogen adsorption-desorption isotherms, powder X-ray diffraction (XRD), FT-IR, TEM, dynamic light scattering (DLS) and zeta potential. FIGS. 2A-2D show transmission electron microscopy (TEM) images of various functionalized MSN. From the TEM images, it can be observed that the MSN particles possess well-ordered mesoporous structures and the average particle size obtained from TEM images is about 40 nm.

Cell Viability and Growth Inhibition Assay.

The WST-1 assay was applied to measure the cell viability and growth inhibition assay: 2×10$^4$ HeLa cells per well were seeded in 24-well plates for 16 h for HeLa cell viability assay. HeLa cells were incubated in serum-free medium containing different amounts of MSN-PEG$_{3.4k}$-Ab-TAT (100 µg/mL) for 4 h. For head and neck squamous cell carcinoma (HNSCC) growth inhibition assay, HNSCC cells were seeded in 24-well plates with a density of 4×10$^4$ cells/well for 16 h and incubated with 200 µg/mL of MSN-PEG$_{3.4k}$-Ab(1:24)-TAT, MSN-PEG$_{3.4k}$-TAT or anti-TNF antibody (100 ng/mL) in serum-free medium for 4 h. Following medium replacement with culture medium, HNSCC cells were incubated for further 72 h. For WST-1 assay, HeLa or HNSCC cells were allowed to grow in culture medium containing WST-1 (Clontech) for 4 h at 37° C. The dark red formazan dye generated by the live cells was proportional to the number of live cells and the absorbance at 450 nm was measured using a microplate reader (Bio-Rad, model 680).

The cell viability of the MSN-PEG$_{3.4k}$-Ab-TAT was examined by using WST-1 assay and MSN-PEG$_{3.4k}$-Ab-TAT shows no significant cytotoxicity.

Western Blotting Analysis

Cell lysates were separated on a 10% SDS-PAGE, and the proteins were then electrophoretically transferred to a polyvinylidene difluoride (PVDF) membrane and blocked 1 h at room temperature in blocking buffer [1×Tris-buffered saline (TBS)-0.1% Tween 20, 5% w/v nonfat dry milk]. Membranes were incubated overnight at 4° C. with primary antibodies: NF-κB p65, TNF-α, Lamin B and GAPDH from Santa Cruz Biotechnology (Santa Cruz, Calif.), along with COX-2 from Cayman (Cayman, Ann Arbor, Mich., USA). All primary antibodies were diluted in blocking buffer (NF-κB p65: 1:500, TNF-α: 1:500, Lamin B: 1:3500, GAPDH: 1:5000 and COX-2: 1:500 dilution). The PVDF membranes were extensively washed and incubated with a horseradish peroxidase-conjugated secondary immunoglobulin G antibody (1:2000 dilution, Santa Cruz Biotechnology) for 1 h at room temperature. Immunoreactive bands were visualized with an enhanced chemiluminescence substrate kit (Amersham Pharmacia Biotech, GE Healthcare UK Ltd, Bucks, UK) according to the manufacturer's protocol.

Cellular Response of NF-κB on MSN-PEGs and In Vitro Pull-Down Assay of MSN-PEG$_{3.4k}$-Ab-TAT 100 µg/mL of MSN-APTMS, MSN-PEG$_{2k}$ and MSN-PEG$_{3.4k}$ were treated in HeLa cells for 4 h, and then incubation without or with TNF-α (50 ng/mL), a NF-κB activator, for another 0.5 h. After the cells were harvested, cytosolic and nuclear protein were isolated, the p65 expression level in either cytosol or nucleus was determined by western blotting experiments. For in vitro pull-down assay, the MSN-PEG$_{3.4k}$-Ab-TAT (100 µg/mL) was mixed and incubated with total lysate of HeLa cell at 4° C. for 18 h in vitro. Then, the mixture was centrifuged at 12,000 rpm for 20 mins and the supernatant (10 µL) was assayed for the free p65 expression level by Western blotting.

Figure 3A:
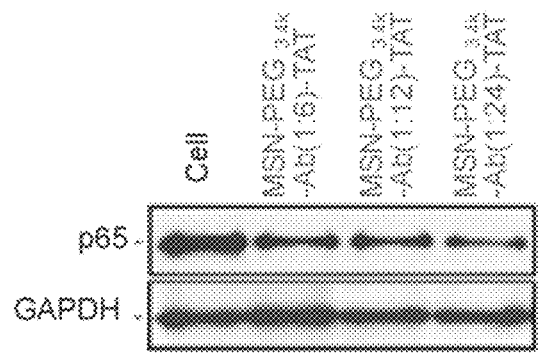
FIGS. 3A-3C show the results of in vitro pull-down assay of various functionalized MSNs.
Figure 3B:
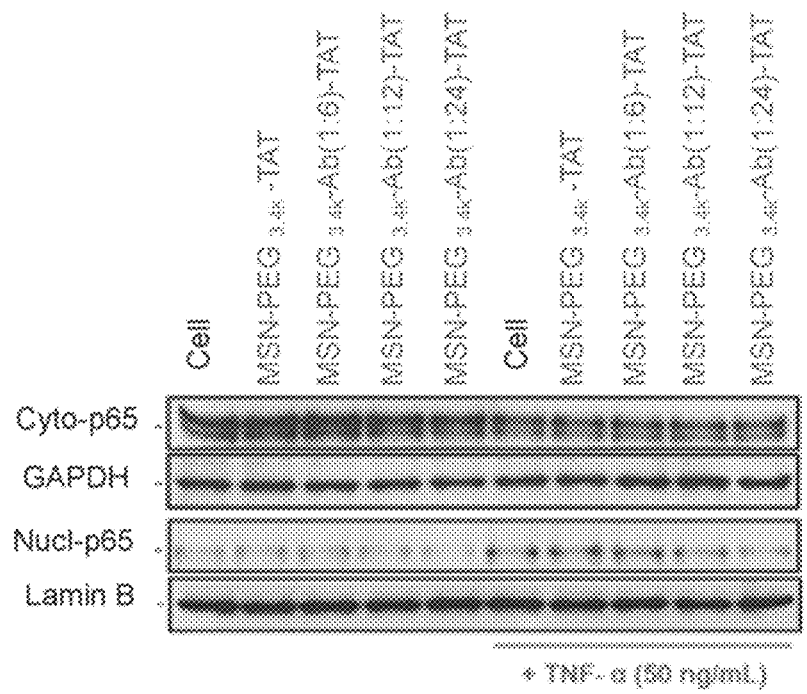
Figure 3C:
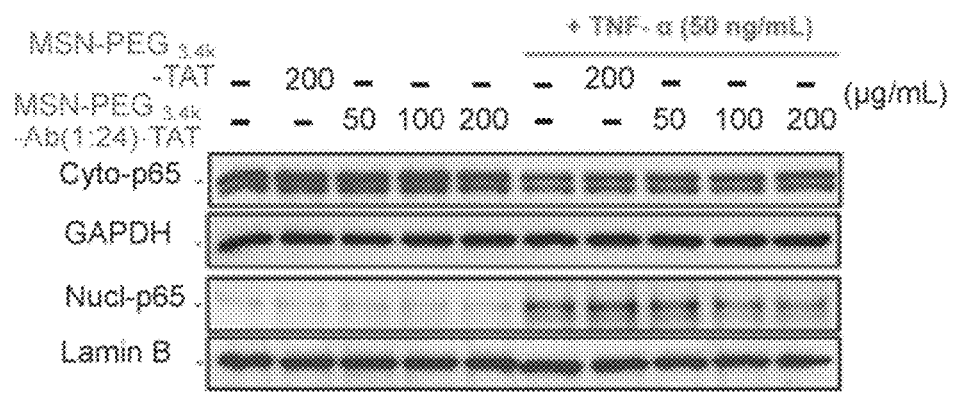

FIGS. 3A-3C show the results of in vitro pull-down assay of various functionalized MSN nanoparticles. MSN-PEG$_{3.4k}$-Ab-TAT blocks NF-κB p65 nuclear translocation and thus inhibits the NF-κB p65 downstream protein expression. HeLa cells were treated with MSN-PEG$_{3.4k}$-TAT or MSN-PEG$_{3.4k}$-Ab-TAT for 4 h at different doses (100 µg/mL for FIG. 3B, 50-200 µg/mL for FIG. 3C). After the delivery, the cells were stimulated with or without 50 ng/mL TNF-α for another 0.5 h. Dose-dependence study of the blockage as shown in FIG. 3C indicates that nuclear p65 level decreases with the increasing concentration of MSN-PEG$_{3.4k}$-Ab(1:24)-TAT.

As shown in FIG. 3B, western blotting was carried out to quantify the p65 level in HeLa cells. After the treatment, the cell lysates were harvested for the p65 level in nucleus and cytoplasm. The western blotting results indicated that MSN-PEG$_{3.4k}$-Ab-TATs did not induce any nuclear translocation of p65 without TNF-α. However, under the TNF-α treatment, a significant increase of p65 level appeared in the nucleus in the absence of MSN-PEG$_{3.4k}$-Ab-TATs. Once the MSN-PEG$_{3.4k}$-Ab-TATs with different amount of conjugated antibody were added, the level of nuclear p65 gradually reduced with increasing amount of antibody. Both MSN-PEG$_{3.4k}$-Ab(1:12)-TAT and MSN-PEG$_{3.4k}$-Ab(1:24)-TAT show obvious suppression of the p65 translocation to the nucleus, whereas MSN-PEG$_{3.4k}$-TAT did not prevent the TNF-α inducing nuclear p65 translocation. Hence, MSN-PEG$_{3.4k}$-Ab-TAT displays the specificity and effectiveness to block NF-κB p65 nuclear translocation through immunogenic binding.

Herein, a nanoparticle/antibody complex targeting NF-κB is employed to catch the Rel protein p65 in the perinuclear region and thus blocking the translocation near the nuclear pore gate. TAT peptide conjugated on mesoporous silica nanoparticles (MSN) help non-endocytosis cell-membrane transducing and converge toward the perinuclear region, where the p65 specific antibody performed the targeting and catching against active NF-κB p65 effectively.

In another embodiment, a protein delivery system combining MSN nanoparticle carriers and one or more denatured fusion proteins has been developed. Such combination of the nanomaterial and one or more fusion proteins not only solves the problems of protein delivery, including chemical solvents, stability, and permeability but also provide a new approach for protein therapy.

Herein, two antioxidant enzyme proteins with similar function for free radicals scavenging, superoxide dismutase (SOD) and glutathione peroxidase (GPx), are demonstrated as the co-delivered enzymes carried by the nanoparticles.

For TAT-SOD and TAT-GPx protein conjugation, the His-tag human Cu, Zn-superoxide dismutase (SOD) and human glutathione peroxidase (GPx) were constructed and overexpressed which contain a human immunodeficiency virus (HIV) transducing domain (TAT, residues 49-57). The sequence of TAT transducing peptide: RKKRRQRRR (SEQ ID NO: 2). The genes of TAT-SOD and TAT-GPx were cloned and inserted into prokaryotic protein expression vector of pQE-30 to form pQE-TAT-SOD and pQE-TAT-GPx. The vectors were transformed into JM109 E. coli and cultured in LB broth with IPTG protein induction for 1 and 3 hours. The TAT-SOD and TAT-GPx with high protein overexpression were displayed by increasing induction time in 10% SDS-PAGE electrophoresis. Finally, the supernatants of pellets of E. coli crude lysates expressed TAT-SOD or TAT-GPx were tried to further directly conjugate in 8M urea.

Synthesis of Fluorescent Mesoporous Silica Nanoparticles (FMSN)

Dye-functionalized MSNs were synthesized by co-condensation process. FITC solution was prepared by dissolving 1 mg of FITC in 5 ml of anhydrous ethanol. 100 μL of APTMS was added with rapid stirring at room temperature in darkness for 24 hours. 0.58 g of $C_{16}TAB$ was dissolved in 300 g of 0.17 M $NH_3$ solution, and 5 mL of dilute TEOS solution (5% v/v TEOS/ethanol) was added with stirring for 5 h. FITC-APTMS solution added before 5 ml of concentrate TEOS solution (25% v/v TEOS/ethanol) was added dropwise with vigorous stirring for 1 h. The solution was then aged at 40° C. for 24 hours to complete the silica condensation. As-synthesized products were collected by centrifugation and washed with 95% ethanol three times. The products called FITC-MSN (FMSN) were stored in absolute ethanol.

Conjugation of NTA-Silane and Ni (II) with FMSN 100 mg of FMSN were suspended in 50 mL of toluene containing 50 mg of NTA-silane and reflux for 18 h. The products were cleaned by ethanol to eliminate excess silane. To remove the $C_{16}TABr$ templates, the particles were dispersed in acidic solution (1 g of HCl in 50 mL ethanol) and stirred at 60° C. for 24 h. Subsequently, hydrolysis of methoxycarbonyl on NTA linker was achieved in the presence of aqueous p-TsOH (0.266 g, pH=2.0) under stirring at 65° C. for 6 h. After cleaned by ethanol, the particles were reacted with 50 mM $NiCl_2$ aqueous solution for 6 h at room temperature. Followed the same cleaned procedure described above, the FMSN-NTA-Ni were obtained and stored in absolute ethanol. FMSN-NTA-Ni with an average loading of Ni content is 0.6 wt % by ICP-MS analysis.

Synthesis of FMSN-PEG/PEI Nanoparticles

Dye-functionalized MSNs were synthesized by co-condensation process. FITC solution was prepared by dissolving 1 mg of FITC in 5 mL of anhydrous ethanol. 100 μL of APTMS was added with rapid stirring at room temperature in darkness for 24 hours. 0.58 g $C_{16}TAB$ was dissolved in 300 g of 0.17 M $NH_3$ solution, and 5 mL of dilute TEOS solution (5% v/v TEOS/ethanol) was added with stirring for 5 h. FITC-APTMS solution added before 5 mL of concentrate TEOS solution (25% v/v TEOS/ethanol) was added dropwise with vigorous stirring for 1 h. 900 μL PEG-silane and 40 μL PEI-silane were added and stirring for 30 mins. The solution was then aged at 40° C. for 24 hours to complete the silica condensation. The solution was aged under hydrothermal condition at 90° C. for 24 hours and 70° C. for 24 hours. As-synthesized products were collected by centrifugation and washed with 95% ethanol. The particle was redispersed in 50 mL of 95% ethanol with 1 g of 37 wt % HCl for 1 hour and then the acid solvent was changed to 50 mL of 95% ethanol with 50 μL of 37 wt % HCl to remove the CTAB. FITC conjugated MSN (FMSN)-PEG/PEI particles were collected by centrifugation and washed with 95% ethanol three times.

Characterization

Transmission electron microscopy (TEM) images were taken on a JEOL JSM-1200 EX II operating at 120 kV. The nickel amount of sample was determined by inductively coupled plasma mass spectrometry (ICP-MS) using Agilent 7700e instrument. Size measurements were performed using dynamic light scattering (DLS) on a Malvern Zetasizer Nano ZS (Malvern, UK). Zeta potential was determined by the electrophoretic mobility and then applying the Henry equation on Malven Zetasizer Nano ZS (Malvern, UK). Table 1 shows dynamic light scattering (DLS) data for average particle size of FMSN-PEG/PEI nanoparticles in different solutions.

TABLE 1

| Solvent | Size (nm) |
| --- | --- |
| $H_2O$ | 65.04 ± 0.57 |
| PBS | 63.03 ± 0.34 |
| DMEM | 63.71 ± 0.80 |
| DMEM + FBS | 69.41 ± 0.40 |

Figure 4A:
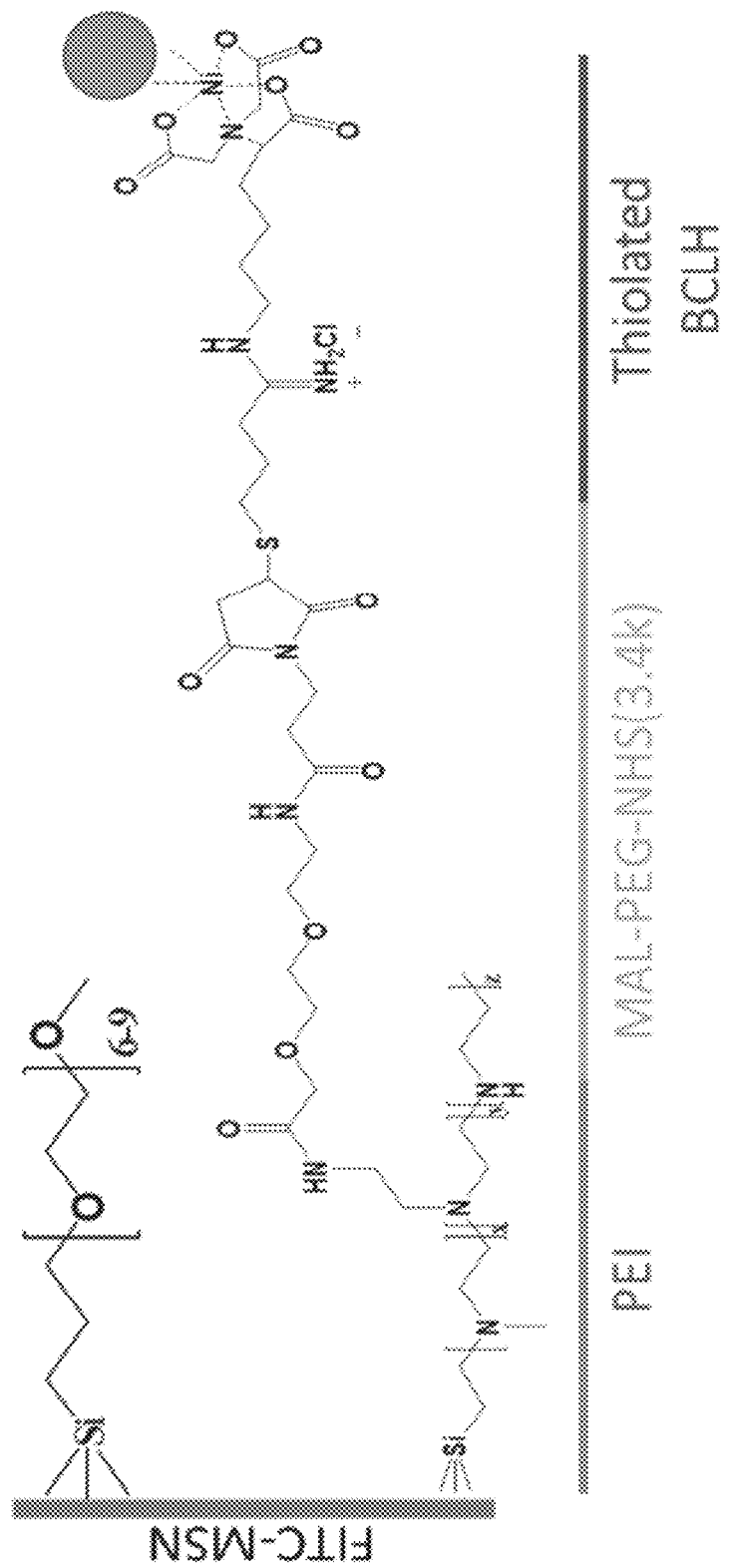
FIG. 4A illustrates the conjugation structure of FMSN-PEG/PEI nanoparticles.
Figure 4B:
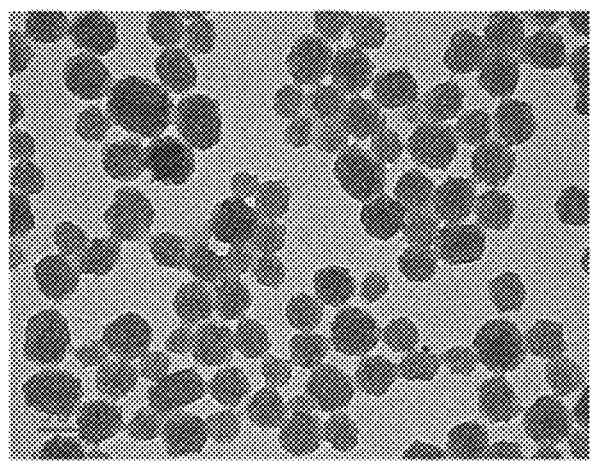
FIG. 4B shows the TEM image of FMSN-PEG/PEI nanoparticles.

FIG. 4A illustrates the conjugation of FMSN-PEG/PEI nanoparticles, while FIG. 4B shows the TEM images of FMSN-PEG/PEI nanoparticles. The TEM images show that these FMSN-PEG/PEI particles possess well-ordered mesoporous structure with an average particle size of about 6070 nm. DLS-determined size indicates very little aggregation in biological solutions (Table 1).

Conjugation of NTA and Ni (II) with FMSN-PEG/PEI 20 mg of FMSN-PEG/PEI was dispersed in 2.5 mL of PBS buffer, and then 6.8 mg of NHS-PEG-MAL (3.4 k) was dissolved in 2.5 mL of PBS and then added to FMSN-PEG/PEI solution. The solution was stirred for 2 hours at room temperature. Thiolated Nα,Nα-Bis(carboxymethyl)-L-lysine hydrate (BCLH) solution was prepared by added 400 μL of Traut's reagent (100 μM) and 5.24 mg of Nα,Nα-Bis(carboxymethyl)-L-lysine hydrate in 5 mL of PBS buffer and stirred for 30 mins. The thiolated BCLH solution was added to the FMSN-PEG/PEI solution and stirred overnight at 4° C. Subsequently, hydrolysis of methoxycarbonyl on NTA linker was achieved in the presence of aqueous ρ-TsOH (0.133 g, pH=2) under stirring at 65° C. for 6 h. After washed by ethanol, the particles were reacted with 50 mM $NiCl_2$ aqueous for 6 h at room temperature. Followed the same washed procedure described above, the FMSN-PEG/PEI-NTA-Ni were obtained and stored in absolute ethanol.

Immobilization of his-TAT-Protein with FMSN-NTA-Ni

The lysate of E. coli containing His-TAT-SOD or His-TAT-GPx was mixed with FMSN-NTA-Ni at 4° C. overnight. Based on the metal affinity between the Ni (II) and His-tag protein offering a tight linkage with a very low dissociation constant, the FMSN-NTA-Ni was directly mixed with TAT-SOD or TAT-GPx protein from the supernatants of pellets of E. coli crude lysates under 8M urea without purifying. The protein-conjugated particles were isolated by centrifugation and washed by ethanol. The protein-functionalized particles were denoted as FMSN-TAT-SOD or FMSN-TAT-GPx.

Determination of SOD and GPx Activity

In the case of SOD, samples were prepared in 300 μL and monitored using a microplate reader (Bio Tek, Synergy™ H1). Firstly, a stock of cocktail reagents containing EDTA ($10^{-4}$ M), cytochrome c ($10^{-5}$ M), and xanthine ($5\times10^{-5}$ M) in 1 mL of 50 mM $K_3PO_4$ was prepared. Then, 280 μL of cocktail reagent was added with various samples, xanthine oxidase (10 μL of 58 mU/mL) and completed with D.I. water up to 300 μL total volume. Finally, 200 μL of each sample was transferred to microplate reader and the absorbance at 550 nm was detection. To measure the SOD activity, the inhibition rate of cytochrome c reduction between native SOD and SOD samples were compared using the slopes of absorbance between t=0 sec and t=180 sec. SOD specific activity was expressed as unit per milligram (U/mg) of total lysate proteins (The Journal of Biological Chemistry, 1969, 244, 6049-6055.).

GPx activity in HeLa cell was measured using the Glutathione Peroxidase Assay Kit (Cayman Chemical), based on the method of Paglia and Valentine, with hydrogen peroxide as a substrate. The method was based on an NADPH-coupled reaction, whereby GPx reduces hydrogen peroxide while oxidizing GSH to GSSG. The generated GSSG is reduced to GSH with consumption of NADPH by GR. Enzyme activity was measured at 340 nm and expressed in units representing oxidation of 1 µmole NADPH per minute per mL sample. GPx specific activity was expressed as unit per milligram (U/mg) of protein.

Cell Viability Assay: $3 \times 10^4$ cells per well were seeded in 24-well plates for proliferation assays. After incubation with different amounts of nanoparticles suspended in serum-free medium for 4 h, respectively, then the 500 µM N, N'-dimethyl-4, 4'-bipyridinium dichloride (paraquat) was added to the culture medium for 24 h. Particle-treated cells were then washed twice with PBS and incubated with 200 µL WST-1 (10%) in DMEM. Cells viability was estimated by a formazan dye generated by the live cells and the absorbance at 450 nm was measured using a microplate reader (Bio-Rad, model 680).

Figure 5A:
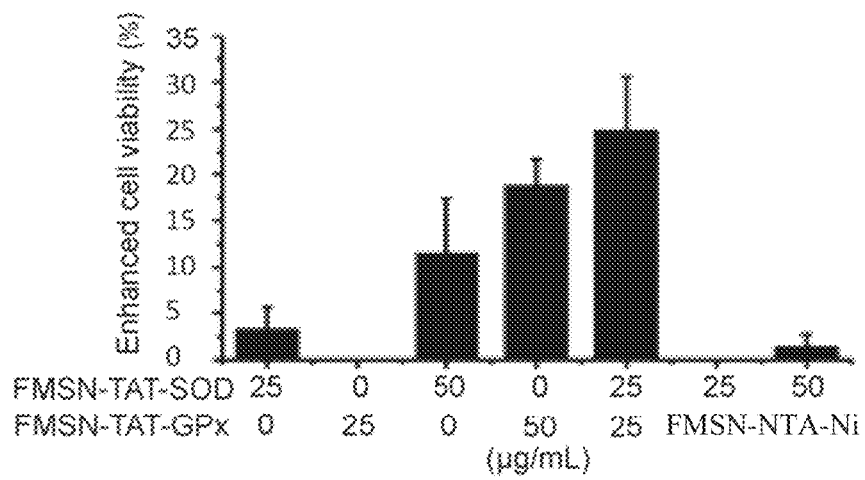
FIGS. 5A-5C illustrate the protection effects of co-delivery of TAT-SOD and TAT-GPx into Hela cells.
Figure 5B:
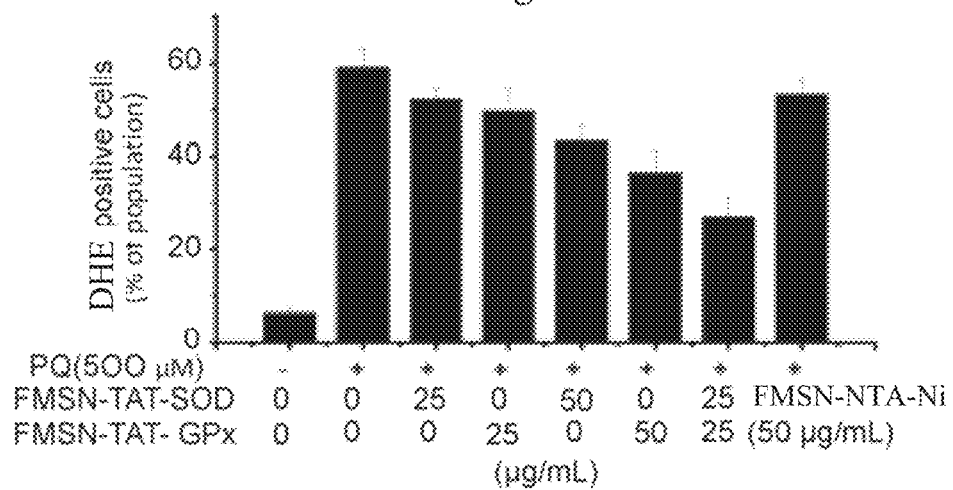
Figure 5C:
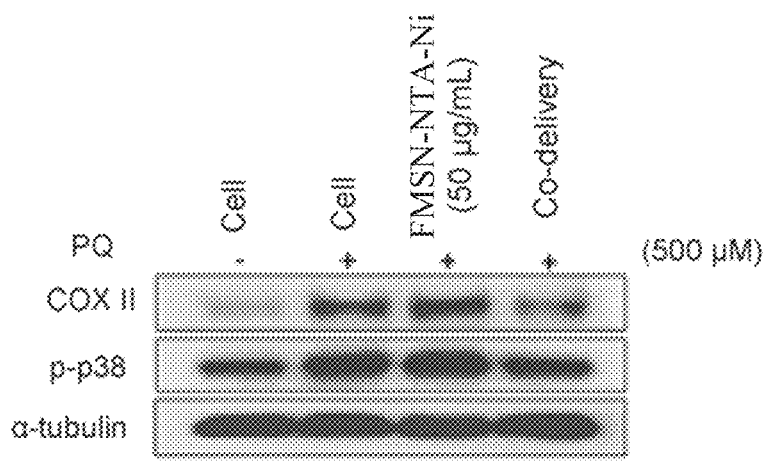

FIGS. 5A-C show the protection effects of co-delivery of TAT-SOD and TAT-GPx into Hela cells. FIG. 5A shows the enhanced cell viability results for various nanoparticles by using WST-1 assay. FIG. 5B shows the results of ROS detection for various nanoparticles. The levels of ROS were stained by DHE assays and quantified by flow cytometry. FIG. 5C shows the results of Western blotting assays to show the levels of COX II and p-p38. The concentration of PQ and co-delivery of FMSN-TAT-SOD and FMSN-TAT-GPx (1:1 ratio) are 500 µM and 25 µg/mL, respectively.

Herein, it is shown that the denatured TAT-SOD or TAT-GPx fusion protein can be co-delivered into Hela cells, and the denatured fusion proteins can be refolded and exhibit the specific enzymatic activities after delivering into the cells. Based on the results shown herein, the TAT-SOD or TAT-GPx fusion protein functionalized FMSN, named as FMSN-TAT-SOD or FMSN-TAT-GPx, still have the enzymatic activity by the refolding mechanism of the cells.

In conclusion, by using MSNs, the silica-based biomolecule carrier of some embodiments can deliver peptides, proteins, enzymes or enzymatic mimetics into the cells as needed and the native activities of the peptides, proteins, enzymes or enzymatic mimetics being delivered into the cell are maintained. The silica-based biomolecule carrier can function as nanoreactors located within the cells and the delivered peptides, proteins, enzymes or enzymatic mimetics can work together to provide multiple functions.

It will be apparent to those skilled in the art that various modifications and variations can be made to the structure of the present invention without departing from the scope or spirit of the invention. In view of the foregoing, it is intended that the present invention covers modifications and variations of this invention provided they fall within the scope of the following claims and their equivalents.

What is claimed is:

1. A silica-based biomolecule carrier, comprising:
   a silica-based porous core;
   a first bioactive moiety;
   a second bioactive moiety functionally associated with the first bioactive moiety; and
   linkers which separately conjugate each of the first bioactive moiety and the second bioactive moiety to the silica-based porous core;
   wherein the first bioactive moiety is an anti-NF-κB (nuclear factor-kappa B) p65 antibody and the second bioactive moiety is a TAT transducing peptide comprising an amino acid sequence selected from: SEQ ID NO. 1 and SEQ ID NO. 2, such that the silica-based biomolecule carrier moves near nuclear membrane and blocks nuclear translocation, and wherein the silica-based porous core has a particle size of at least 40 nm.

2. The silica-based biomolecule carrier of claim 1, wherein at least one of the first bioactive moiety and the second bioactive moiety comprises a cell-penetrating domain.

3. The silica-based biomolecule carrier of claim 1, wherein at least one of the first bioactive moiety and the second bioactive moiety comprises a polyhistidine tag.

4. The silica-based biomolecule carrier of claim 1, wherein at least one of the linkers comprises a polyethylene glycol segment.

5. The silica-based biomolecule carrier of claim 1, wherein at least one of the linkers comprises a bivalent nickel or cobalt ion.

6. The silica-based biomolecule carrier of claim 1, wherein at least one of the linkers is bound to the first bioactive moiety, the second bioactive moiety or both via a covalent bond.

7. The silica-based biomolecule carrier of claim 1, wherein at least one of the linkers comprises a first terminal linked to the porous silica-based core, a second terminal linked to the first or second bioactive moiety, and a functional segment between the first terminal and the second terminal for facilitating cellular uptake.

8. The silica-based biomolecule carrier of claim 1, wherein the silica-based porous core is functionalized with polyethylenimine, amino groups, nitrilotriacetic acid, polyethylene glycol, fluorescent tags or a combination thereof.

9. The silica-based biomolecule carrier of claim 1, wherein the silica-based porous core has an average pore size of 2 to 50 nm.

10. The silica-based biomolecule carrier of claim 1, wherein the silica-based porous core has a particle size of less than 300 nm.

11. A pharmaceutical composition comprising a plurality of silica-based biomolecule carriers of claim 1 dispersed in a biological medium.

12. A method of preparing a composition comprising a silica-based biomolecule carrier, comprising:
providing a silica-based carrier having a porous core;
forming linkers on the silica-based porous core;
conjugating first biomolecules to the silica-based porous core via at least a part of the linkers; and
conjugating second biomolecules functionally associated with the first biomolecules to the silica-based porous core via at least a part of the linkers; and
forming the silica-based biomolecule carrier, the silica-based biomolecule carrier comprising a first bioactive moiety, which is formed by linking the first biomolecules to the silica-based porous core, and a second bioactive moiety, which is formed by linking the second biomolecules to the silica-based porous core;
wherein the first bioactive moiety is an anti-NF-κB (nuclear factor-kappa B) p65 antibody and the second bioactive moiety is a TAT transducing peptide comprising an amino acid sequence selected from: SEQ ID NO. 1 and SEQ ID NO. 2, such that the silica-based carrier moves near nuclear membrane and blocks nuclear translocation, and wherein the silica-based porous core has a particle size of at least 40 nm.

* * * * *